United States Patent
Wang et al.

(10) Patent No.: US 9,547,974 B2
(45) Date of Patent: Jan. 17, 2017

(54) DEVICE FOR DETECTING BLOCKAGE OF AIR FILTER MESH

(71) Applicant: Zhongshan Broad-Ocean Motor Co., Ltd., Zhongshan (CN)

(72) Inventors: Jizhong Wang, Zhongshan (CN); Yiqiao Zhou, Zhongshan (CN); Zheng Zhang, Zhongshan (CN); Xiansheng Zhang, Zhongshan (CN); Hairong Sun, Zhongshan (CN); Yong Zhao, Zhongshan (CN)

(73) Assignee: ZHONGSHAN BROAD-OCEAN MOTOR CO., LTD., Zhongshan (CN)

( * ) Notice: Subject to any disclaimer, the term of this patent is extended or adjusted under 35 U.S.C. 154(b) by 0 days.

(21) Appl. No.: 14/986,715

(22) Filed: Jan. 3, 2016

(65) Prior Publication Data
US 2016/0117907 A1    Apr. 28, 2016

Related U.S. Application Data

(63) Continuation-in-part of application No. PCT/CN2014/088272, filed on Oct. 10, 2014.

(30) Foreign Application Priority Data

Aug. 30, 2014    (CN) .......................... 2014 1 0439148

(51) Int. Cl.
*G08B 21/00*    (2006.01)
*G08B 21/18*    (2006.01)
(Continued)

(52) U.S. Cl.
CPC ............... *G08B 21/182* (2013.01); *F24F 1/00* (2013.01); *F24F 11/00* (2013.01); *G01D 5/142* (2013.01);
(Continued)

(58) Field of Classification Search
CPC ............ G08B 21/182; G08B 5/22; F24F 1/00; F24F 11/00; G01M 1/00; G01F 15/061; G01F 9/00; G01N 15/082; G01N 2015/084; G01D 5/142
(Continued)

(56) References Cited

U.S. PATENT DOCUMENTS 6,448,896 B1 *  9/2002  Bankus .............. B01D 46/0086
                                                      236/49.3
6,842,117 B2 *  1/2005  Keown ................ B01D 35/143
                                                      340/606

(Continued)

*Primary Examiner* — Anh V La
(74) *Attorney, Agent, or Firm* — Matthias Scholl, PC; Matthias Scholl

(57) ABSTRACT

A device for detecting blockage of an air filter mesh, including: an air inlet, an air outlet, an air duct, a fan or a wind wheel, a blower motor, an air filter mesh, and a controller. The controller includes a main control board including: a microprocessor, an inverter circuit, and a motor operation parameter detecting circuit. The air filter mesh is disposed in the air duct. The motor operation parameter detecting circuit inputs a real time operation parameter into the microprocessor, and the output terminal of the microprocessor controls the inverter circuit. A function module of the microprocessor calculates a detected air volume according to the real time operation parameter. When the detected air volume is smaller than a preset air volume, the microprocessor determines that the air filter mesh is obstructed and outputs a signal to an alarm circuit to trigger an alarm.

17 Claims, 13 Drawing Sheets

(51) Int. Cl.
*F24F 11/00* (2006.01)
*G01D 5/14* (2006.01)
*G01F 15/06* (2006.01)
*G01N 15/08* (2006.01)
*G08B 5/22* (2006.01)
*F24F 1/00* (2011.01)
*G01M 1/00* (2006.01)
*G01F 9/00* (2006.01)

(52) U.S. Cl.
CPC .............. *G01F 15/061* (2013.01); *G01M 1/00* (2013.01); *G01N 15/082* (2013.01); *G08B 5/22* (2013.01); *G01F 9/00* (2013.01); *G01N 2015/084* (2013.01)

(58) Field of Classification Search
USPC .. 340/607, 606, 610, 608, 609, 603; 55/311, 55/323, 327; 73/28.03, 28.01; 454/96, 454/111, 158, 191, 193
See application file for complete search history.

(56) References Cited

U.S. PATENT DOCUMENTS 8,334,783 B2* 12/2012 Katayama .............. G03B 21/16
340/607
2007/0146148 A1* 6/2007 Kawasaki .......... B01D 46/0086
340/607

* cited by examiner

DEVICE FOR DETECTING BLOCKAGE OF AIR FILTER MESH

CROSS-REFERENCE TO RELATED APPLICATIONS

This application is a continuation-in-part of International Patent Application No. PCT/CN2014/088272 with an international filing date of Oct. 10, 2014, designating the United States, now pending, and further claims priority benefits to Chinese Patent Application No. 201410439148.5 filed Aug. 30, 2014. The contents of all of the aforementioned applications, including any intervening amendments thereto, are incorporated herein by reference.

BACKGROUND OF THE INVENTION

Field of the Invention

The invention relates to a device for detecting blockage of an air filter mesh.

Description of the Related Art

Typically, to monitor the air volume of an air conditioning system, an anemometer or an air volume meter is installed at the air outlet or in the air duct. However, to achieve the monitoring, additional hardware and complex wiring are required, which increases the production cost.

In addition, a typical DC motor is equipped with a motor controller, and the motor body together with the motor controller is installed in the air duct, which occupies relatively large space of the air duct and reduces the ventilation efficiency. The DC motor often has large size and is difficult to install, and the motor controller has high cost.

SUMMARY OF THE INVENTION

In view of the above-described problems, it is one objective of the invention to provide a device for detecting blockage of an air filter mesh. The blower motor of the device is equipped with no motor controller and acts as a unit for detecting the air volume. The microprocessor, the inverter circuit, and the motor operation parameter detecting circuit are arranged on the controller of the device. When the detected air volume is smaller than the preset air volume, it is determined that the air filter mesh is obstructed and the alarming signal is output. No additional hardware is required, the structure is simple and compact, the installation is convenient, and the production cost is low.

To achieve the above objective, in accordance with one embodiment of the invention, there is provided a device for detecting blockage of an air filter mesh. The device comprises: an air inlet, an air outlet, an air duct, a fan or a wind wheel, a blower motor, an air filter mesh, and a controller. The blower motor comprises: a rotating shaft, a permanent magnetic rotor assembly, a stator assembly, and a housing assembly. The stator assembly comprises a stator core and a coiling winding. The controller comprises a main control board comprising: a microprocessor, an inverter circuit, and a motor operation parameter detecting circuit. The inverter circuit comprises an output terminal. The microprocessor comprises an output terminal and a function module for calculating an air volume. The air filter mesh is disposed in the air duct. The blower motor drives the fan or the wind wheel to rotate to allow the air to enter the air duct via the air inlet, pass through the air filter mesh, and exit the air duct via the air outlet. The blower motor is a motor body excluding a controller. The permanent magnetic rotor assembly and the stator assembly form magnetic coupling. The coiling winding is wound on the stator core. The output terminal of the inverter circuit is connected to the coil winding. The motor operation parameter detecting circuit inputs a real time operation parameter into the microprocessor, and the output terminal of the microprocessor controls the inverter circuit. The function module calculates a detected air volume according to the real time operation parameter. When the detected air volume is smaller than a preset air volume, the microprocessor determines that the air filter mesh is obstructed and outputs a signal to an alarm circuit to trigger an alarm.

In a class of this embodiment, the device is a split air conditioner, a cabinet air conditioner, a window air conditioner, a multi-connected air conditioner, a wind pipe air conditioner, a commercial coil air conditioner, a ceiling air conditioner, a heating, ventilating, and air conditioning system, a living air device, an air cleaner, or a soot absorber.

In a class of this embodiment, the real time operation parameter of the motor comprises: a phase current and a rotor position signal; or a bus current and a rotor position signal; or a bus current, a bus voltage, and a rotor position signal.

In a class of this embodiment, a function for calculating the air volume is Q=F(POWER, n), in which, POWER represents an input power of the motor and is calculated by the bus current and the bus voltage of the motor, n represents a rotational speed of the motor and is calculated by the rotor position signal.

In a class of this embodiment, the blower motor operates in a mode of constant air volume control. The microprocessor firstly measures a real time power to determine whether the real time power reaches a rated power. When the real time power reaches the rated power and a difference between the detected air volume and the preset air volume reaches a certain value, the alarm is triggered. When the difference between the detected air volume and the preset air volume is within a permitted range, the alarm is not triggered.

In a class of this embodiment, the blower motor operates in a mode of constant torque control, and when a difference between the detected air volume and the preset air volume reaches a certain value, it is determined that the air filter mesh is obstructed and the alarm is triggered.

In a class of this embodiment, the blower motor operates in a mode of constant rotational speed control, and when a difference between the detected air volume and the preset air volume reaches a certain value, it is determined that the air filter mesh is obstructed and the alarm is triggered.

In a class of this embodiment, the main control board is a control board of the air conditioning system. The microprocessor of the main control board is connected to a compressor and an expansion valve via an interface circuit for controlling the compressor and the expansion valve.

In a class of this embodiment, the alarm circuit is an audio alarm circuit or a photoelectric alarm circuit.

In a class of this embodiment, the alarm circuit comprises a liquid crystal display. The microprocessor outputs a signal to the liquid crystal display to indicate that the air filter mesh is obstructed in the form of characters or figures.

In a class of this embodiment, the motor body further comprises a Hall circuit for detecting a rotor position signal.

Advantages according to embodiments of the invention are summarized as follows:

1) The blower motor of the device is equipped with no motor controller and acts as a unit for detecting the air volume, the microprocessor, the inverter circuit, and the motor operation parameter detecting circuit are arranged on the controller of the device. When the detected air volume is smaller than the preset air volume, it is determined that the air filter mesh is obstructed and the alarming signal is output. No additional hardware is necessitated, the structure is simple and compact, the installation is convenient, and the production cost is low.

2) The blower motor operates in the control mode of the constant air volume. The microprocessor firstly measures the real time power to determine whether the real time power reaches the rated power. When the real time power reaches the rated power, the difference between the detected air volume and the preset air volume is then determined. The technical solution is simple, the computation amount of the microprocessor is small, and the practicability is high.

3) The alarm circuit comprises the liquid crystal display of the device. The microprocessor first sends the alarming signal to the control board, and the control board outputs a signal to the liquid crystal display to indicate that the air filter mesh is obstructed in the form of characters or figures. The existing source and the friendly interface of the air conditioning system are fully utilized to trigger the alarm, so that the production cost is saved.

BRIEF DESCRIPTION OF THE DRAWINGS

The invention is described hereinbelow with reference to the accompanying drawings, in which.

DETAILED DESCRIPTION OF THE EMBODIMENTS

Figure 1:
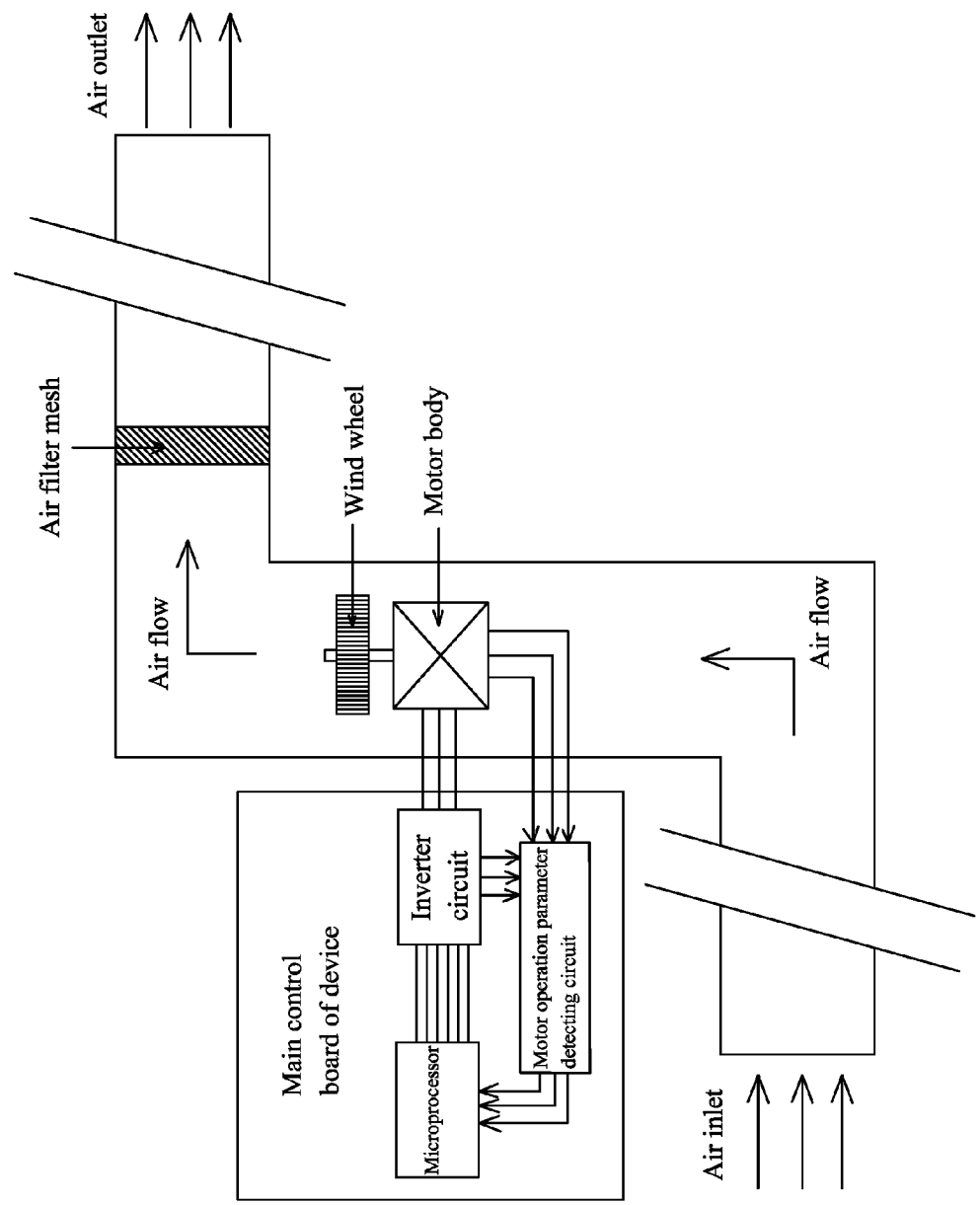
FIG. 1 is a structure diagram of a conventional air conditioning blower system.

For further illustrating the invention, experiments detailing a device for detecting blockage of an air filter mesh are described hereinbelow combined with the drawings.

Example 1

A device for detecting blockage of an air filter mesh, the device comprises: an air inlet, an air outlet, an air duct, a fan or a wind wheel, a blower motor, an air filter mesh, and a controller. The air filter mesh is disposed in the air duct; the blower motor drives the fan or the wind wheel to rotate to allow the air to enter the air duct via the air inlet, pass through the air filter mesh, and exit the air duct via the air outlet.

The blower motor is a motor body excluding a controller and comprises: a rotating shaft, a permanent magnetic rotor assembly, a stator assembly, and a housing assembly. The permanent magnetic rotor assembly and the stator assembly form magnetic coupling. The stator assembly comprises a stator core and a coiling winding wound on the stator core.

The controller comprises a main control board, and the main control board comprises: a microprocessor, an inverter circuit, and a motor operation parameter detecting circuit. An output terminal of the inverter circuit is connected to the coil winding. The motor operation parameter detecting circuit inputs a real time operation parameter into the microprocessor, and an output terminal of the microprocessor controls the inverter circuit. The microprocessor comprises a function module for calculating an air volume, and the function module calculates a detected air volume according to the real time operation parameter.

When the detected air volume is smaller than a preset air volume, the microprocessor determines that the air filter mesh is obstructed and outputs a signal to an alarm circuit to trigger an alarm.

The device is a split air conditioner, a cabinet air conditioner, a window air conditioner, a multi-connected air conditioner, a wind pipe air conditioner, a commercial coil air conditioner, a ceiling air conditioner, a heating, ventilating, and air conditioning system, a living air device, an air cleaner, or a soot absorber. The real time operation parameter of the motor comprises: a phase current and a rotor position signal; or a bus current and a rotor position signal; or a bus current, a bus voltage, and a rotor position signal. A function for calculating the air volume is $Q=F(POWER, n)$, in which, POWER represents an input power of the motor, and n represents a rotational speed of the motor. The blower motor operates in a mode of constant air volume control. The microprocessor firstly measures a real time power to determine whether the real time power reaches a rated power. When the real time power reaches the rated power and a difference between the detected air volume and the preset air volume reaches a certain value, the alarm is triggered. When the difference between the detected air volume and the preset air volume is within a permitted range, the alarm is not triggered. The blower motor operates in a mode of constant torque control, and when a difference between the detected air volume and the preset air volume reaches a certain value, it is determined that the air filter mesh is obstructed and the alarm is triggered. The blower motor operates in a mode of constant rotational speed control, and when a difference between the detected air volume and the preset air volume reaches a certain value, it is determined that the air filter mesh is obstructed and the alarm is triggered.

Circuit structure of the blower motor and measuring and controlling principle of the function module for calculating the air volume are introduced as follows:

As shown in FIG. 1, a blower system (e.g., a gas furnace or an air processor) which is replaced with "motor+wind wheel" in the figure is installed in a typical air-conditioning air duct. An air filter mesh is also disposed in the air duct. When the motor is started, the air is blasted. The number of air inlets and air outlets are related to the room number, no unified standards exist in the design of the air duct, and the air filter meshes may have different pressure drops, so that the actual air volume of the conventional blower system comprising a signal phase AC motor-PSC motor varies when the blower system is installed in different air ducts. The blower motor in the invention is the BLDC motor or the ECM motor.

Figure 2:
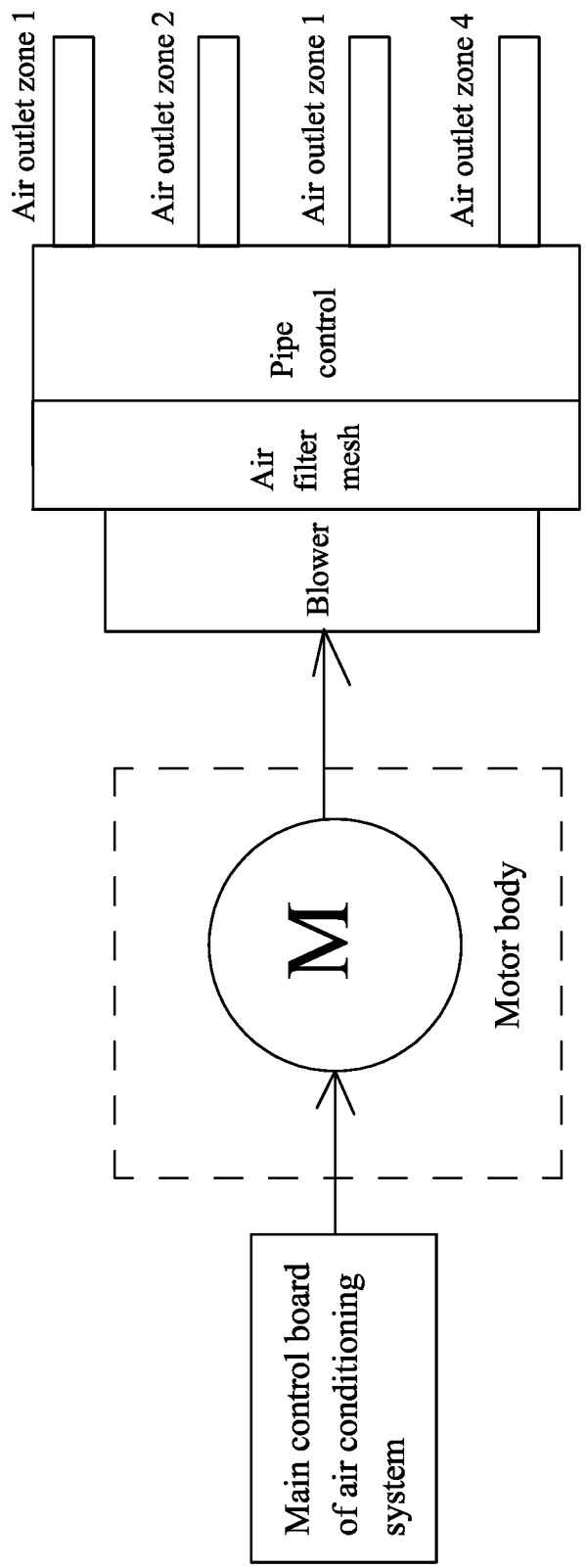
FIG. 2 is a schematic diagram showing a blower motor mounted in an air conditioning system in accordance with one embodiment of the invention.

As shown in FIG. 2, 1) the product is controlled by a controller of the air conditioning system. The controller of the air conditioning system controls all operating devices of the product. The controller of the air conditioning system comprises a microprocessor, such as an MCU or a DSP electric board for controlling the motor. A power supply supplies power to each part of the circuit of the controller and is formed by setting a DC bus voltage and a DC bus current. Thus, the control of the motor requires power transportation. A parallel resistance circuit is generally employed as hardware for sensing the current and the voltage and as a feedback of the system to control the motor driver and execute the motor controller, such as a vector control, a direct torque control, or other control mode in the absence or presence of the sensor. It is well known that any variation of the running period of an electronic component is the factor affecting the measurement accuracy and the persistence. 2) A rotor of the blower motor is provided with permanent magnets, and a stator assembly is provided with multi-phase coil windings. When the temperature varies, the permanent magnets and the resistance of the coil windings changes, which possibly leads to the change of the motor control. The manufacture process of the motor also generates certain variations in the aging of the motor, the new and the old motor, the accuracy and the endurance controlled by contributing factors, and the service life, and variation of the magnetic flux of the magnets of the motor and demagnetization may occur due to the temperature variation. In addition, the malfunction of the motor shaft may occur, and the security of the system needs to be detected and monitored in real-time. 3) The blower is mounted on the shaft of the motor and air flow is produced at a certain speed during rotation. The mounting position may affect the operation, increase the friction, decrease the flow rate, or even result in the mistake rotating direction. 4) The air filter mesh must be replaced and maintained periodically, which however cannot be traced for a long turn and may increase the friction and affect the flow pressure. 5) Pipe control: the pipe system may changes the factors such as the regional control and the pressure variation of the on/off state of the ventilation ports due to the dust and the pipe rupture. Thus, multiple variable factors may be produced during the constant air volume control according to the actual circumstance.

Figure 3:
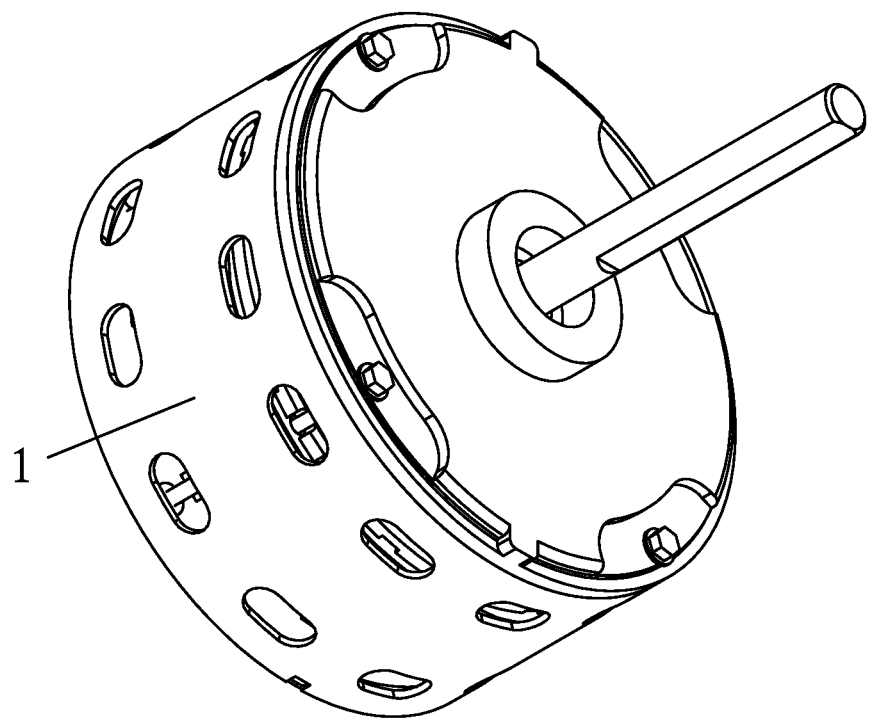
FIG. 3 is a stereogram of a blower motor in accordance with one embodiment of the invention.
Figure 4:
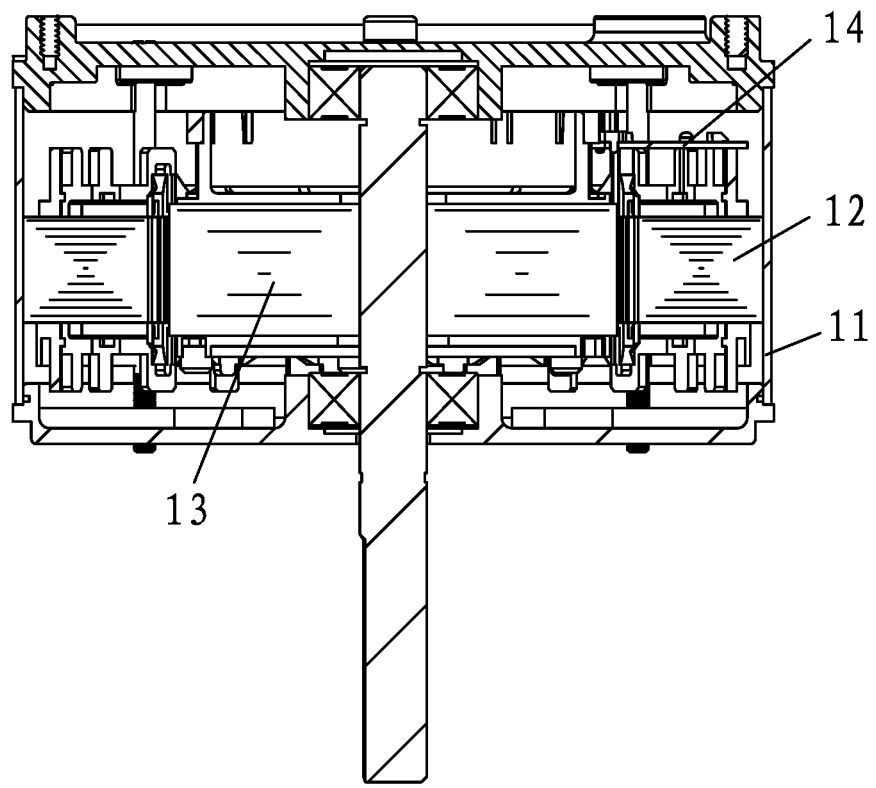
FIG. 4 is a sectional view of a motor blower in accordance with one embodiment of the invention.
Figure 5:
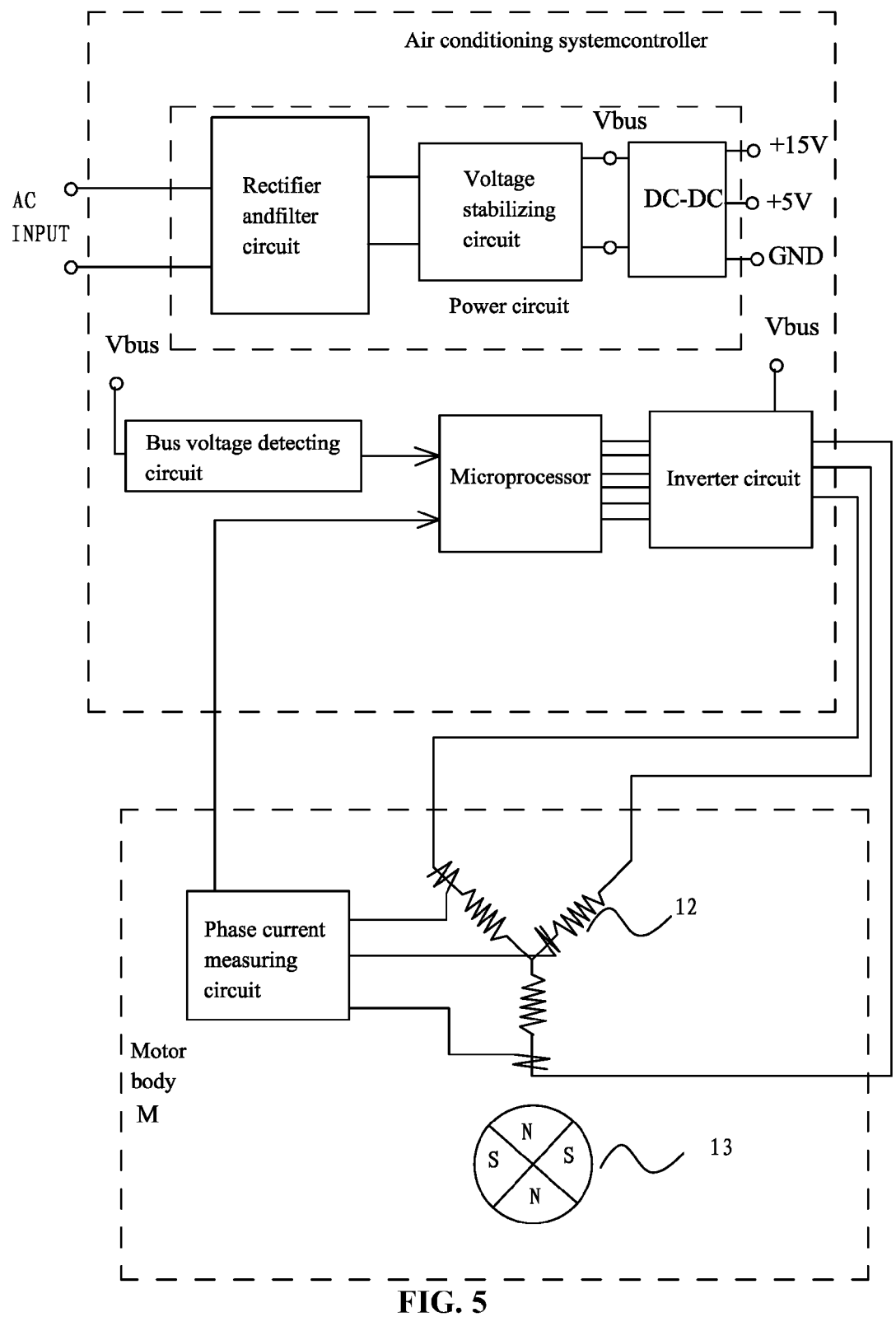
FIG. 5 is a circuit block diagram of a blower motor in accordance with one embodiment of the invention.

As shown in FIGS. 3-5, the blower motor comprises a motor controller 1 and a motor body 1. The motor body 1 comprises: a stator assembly 12, a rotor assembly 13, and a housing assembly 11. The stator assembly is mounted on the housing assembly 11. The motor body 1 is provided with a Hall sensor 14 for detecting a rotor position. The rotor assembly 13 is nested inside or outside the stator assembly 12.

The controller of the air conditioning system comprises: a power circuit, a microprocessor, a bus current detecting circuit, an inverter circuit, and a rotor position measuring circuit 14 (the Hall sensor). The power circuit supplies power for each circuit part. The rotor position measuring circuit is configured to detect a rotor position signal and input the rotor position signal to the microprocessor. The bus current detecting circuit inputs the detected bus current into the microprocessor, and the bus voltage detecting circuit inputs the DC bus voltage into the microprocessor. The microprocessor controls the inverter circuit, and the inverter circuit controls the power-on and power-off state of each phase of coil windings by controlling the stator assembly 12.

Figure 6:
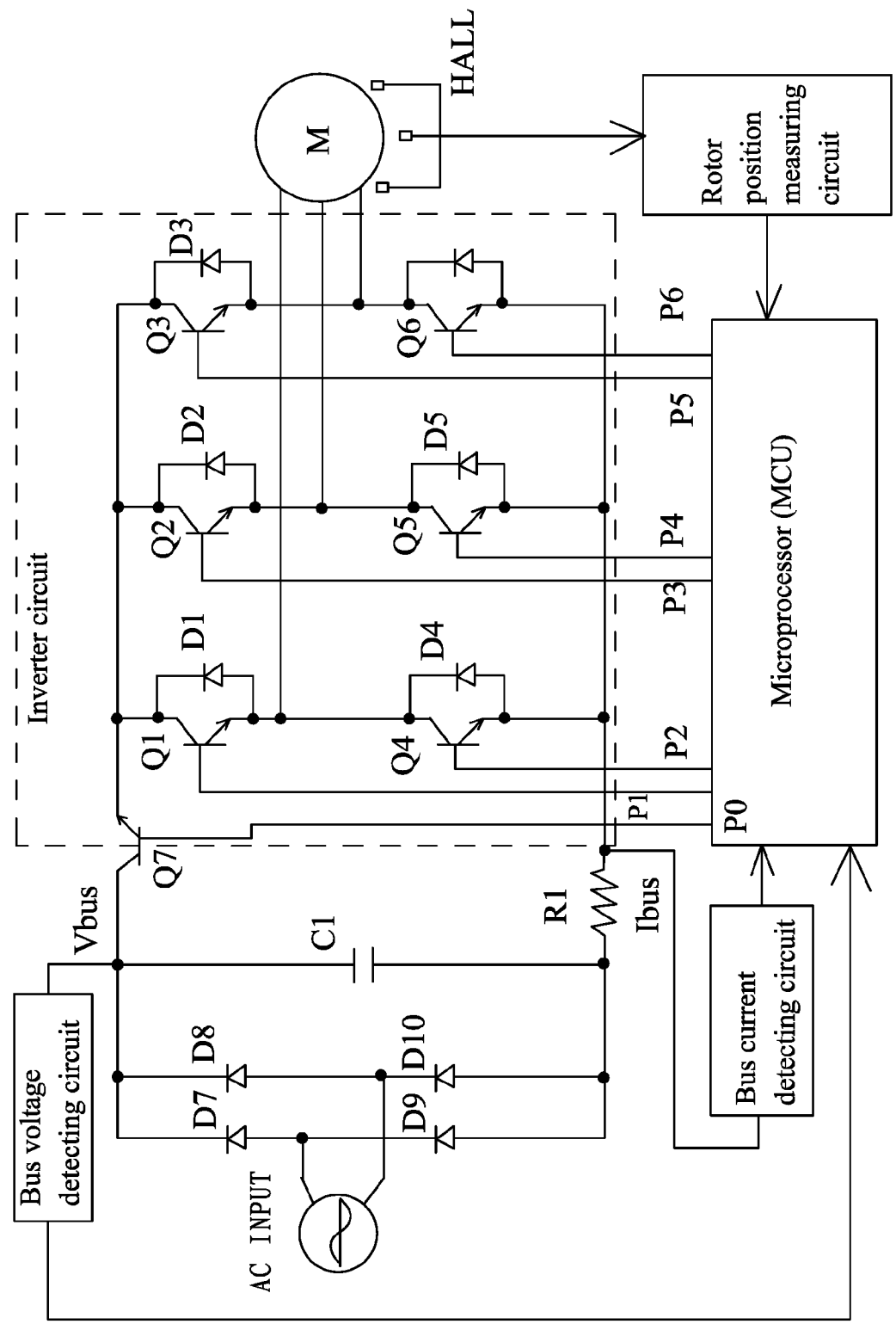
FIG. 6 is a circuit diagram corresponding to FIG. 5.

As shown in FIGS. 5-6, given that the blower motor is a three-phase brushless DC permanent synchronous motor, the rotor position measuring circuit 14 generally adopts three Hall sensors. Each of the three Hall sensors respectively detects a rotor position in a 360° electric angle cycle, and an energization state of each phase of the coil winding of the stator assembly changes when the electric angle changes for every 120 degrees, thereby forming the three-phase six-step control mode. An AC input passes a full wave commutate circuit formed by diodes D7, D8, D9, and D10 and outputs a DC bus voltage Vbus at a terminal of a capacitance C1. The DC bus voltage Vbus is related to an input AC voltage, and when a voltage of the AC input is determined, a line voltage UP of the three-phase winding is a PWM chopped output voltage, UP=Vbus*w, in which, w represents a duty ratio of the PWM signal input into the inverter circuit by the microprocessor. The line voltage UP can be changed by changing the DC bus current Ibus. The inverter circuit is formed by electronic switching tubes Q1, Q2, Q3, Q4, Q5, and Q6, and control terminals of the electronic switching tubes Q1, Q2, Q3, Q4, Q5, and Q6 are controlled by six paths of PWM signals (P1, P2, P3, P4, P5, and P6) output by the microprocessor. The inverter circuit is further connected to a resistance R1 for detecting the bus current Ibus, and the bus current Ibus detected by the resistance R1 is converted by the bus current detecting circuit and transmitted to the microprocessor. An input power of the motor is controlled by an electronic switching tube Q7, and a conduction time of the electronic switching tube Q7 is controlled by one path of PWM signal $P_0$ output by the microprocessor so as to control the input power of the motor.

Figure 7:
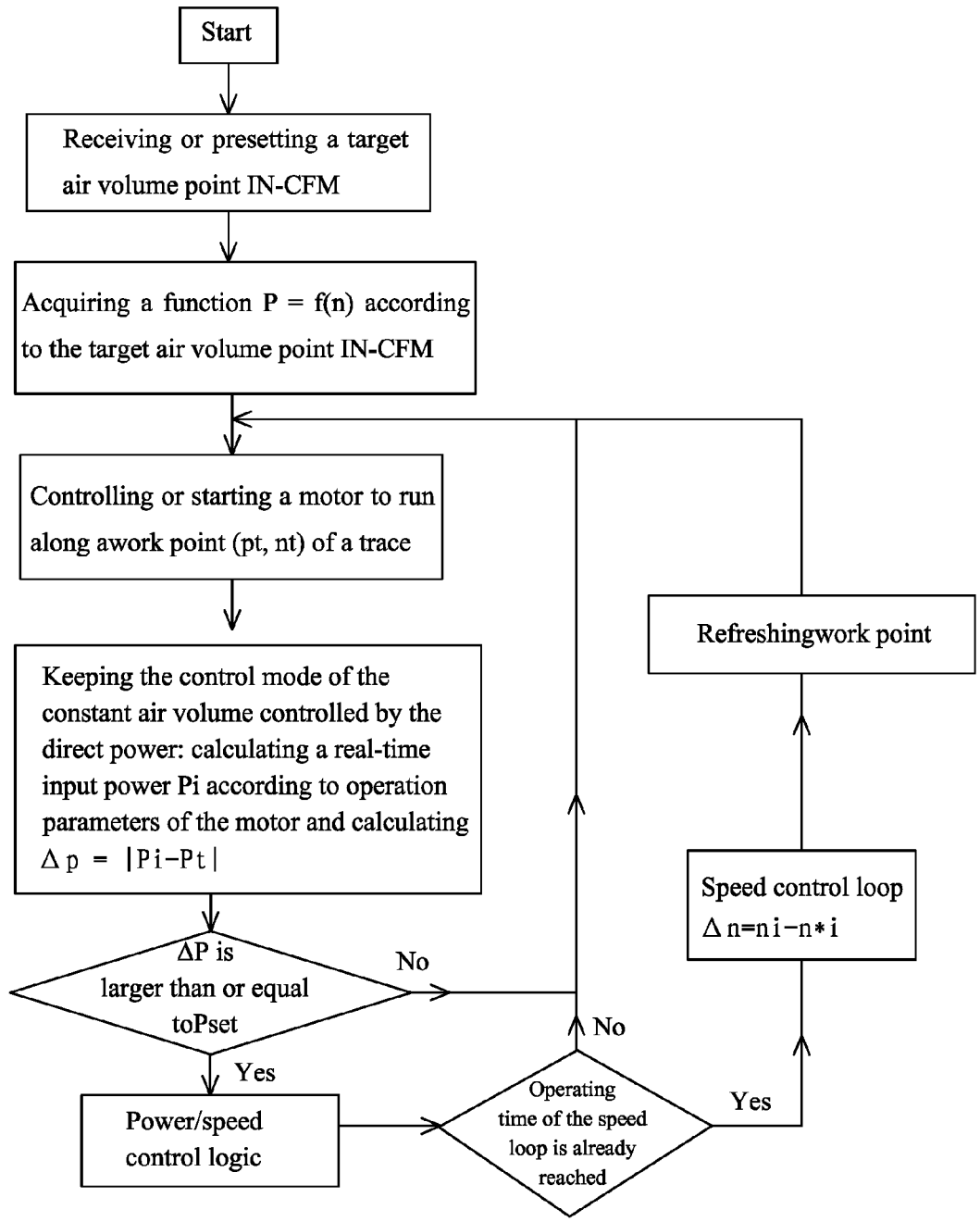
FIG. 7 is a flow chart illustrating a method for controlling a constant air volume of a blower motor in accordance with one embodiment of the invention.

As shown in FIG. 7, a method for controlling a constant air volume of a blower motor in an air conditioning system by direct power control is illustrated. The blower motor drives a wind wheel and comprises: a stator assembly, a permanent magnet rotor assembly, and a motor controller. The controller of the air conditioning system comprises: a microprocessor, an inverter circuit, a rotor position measuring circuit, a bus current detecting circuit, a bus voltage detecting circuit, and an input power control circuit (not shown in the figure). The signal of the rotor position is detected by the rotor position measuring circuit, and a real-time rotational speed n of the motor is calculated by the microprocessor according to the signal of the rotor position. The bus current is input into the microprocessor by the bus current detecting circuit, and the DC bus voltage is input into the microprocessor by the bus voltage detecting circuit. The inverter circuit is controlled by the microprocessor. The power-on and power-off state of each phase of the coil windings of the stator assembly is controlled by the inverter circuit, and the input power control circuit is controlled by the microprocessor. The method comprises the following steps:

A) starting the motor controller, receiving or presetting an target air volume point IN-CFM;

B) acquiring a function P=f(n) according to the target air volume point IN-CFM, in which, n represents the rotational speed, and P represents the input power of the motor.

C) entering the control mode of the constant air volume controlled by the direct power: starting the motor when the rotational speed of the motor is zero, allowing the motor to reach a stable work point $(p_t, n_t)$ along a control trace of the function P=f(n), in which $p_t, n_t$ is a pair of input power and rotational speed satisfying the trace of the function P=f(n) involving the constant air volume control;

D) keeping the control mode of the constant air volume controlled by the direct power: calculating a real-time input power $P_i$ according to operation parameters of the motor and calculating $\Delta P=|Pt-Pi|$;

E) keeping the current work point when a power increase $\Delta P$ is smaller than a preset value $P_{set}$;

F) when the power increase $\Delta P$ is larger than the preset value $P_{set}$, determining by calculation of power/rotational speed control logic whether an operating time of a speed loop is reached; and when the operating time of the speed loop is not reached, keeping the current work point;

G) when the operating time of the speed loop is already reached, entering a speed control loop and regulating the speed according to $\Delta n=|ni-nt|$, in which, $n_i$ represents a real-time rotational speed, reaching a new work point $(P_i, n_i)$, that is, $P_t=P_i$, and $n_t=n_i$, and return C).

The function Pi=F(n) is acquired as follows: for multiple target air volumes, allowing the motor to operate at a constant rotational speed, regulating a static pressure from a lower boundary to an upper boundary which covers an actual static pressure range in an air duct device, and then regulating the rotational speed n and a real-time input power $P_i$ of the motor to keep the target air volume, and recording the rotational speed n at the stable state of the motor and the corresponding real-time input power $P_i$, whereby obtaining a group of the rotational speed n and the real-time input power $P_i$ for each of the M target air volumes, and establishing the function Pi=F(n) for each target air volume by curve fitting.

When the target air volume point IN-CFM input from the external is not equal to any of the multiple target air volume, a function of P=f(n) corresponding to any of the target air volume points IN-CFM input from the external is calculated by fitting via interpolation method, thereby realizing the constant air volume control for any target air volume in the entire process.

The function P=f(n) is a polynomial function, $P=C_1+C_2\times n+ \ldots +C_m\times n^{m-1}$, in which $C_1, C_2 \ldots, C_m$ represent coefficients, n represents the rotational speed of the motor. Each target air volume corresponds to a group of coefficients $C_1, C_2 \ldots, C_m$ and the corresponding relations are stored. A corresponding group of the coefficients $C_1, C_2 \ldots, C_m$ are acquired by the microprocessor according to the input target air volume points IN-CFM by a look-up table method and the interpolation method.

The function P=f(n) is a second order function $P=C_1+C_2\times n+C_3\times n^2$.

Figure 8:
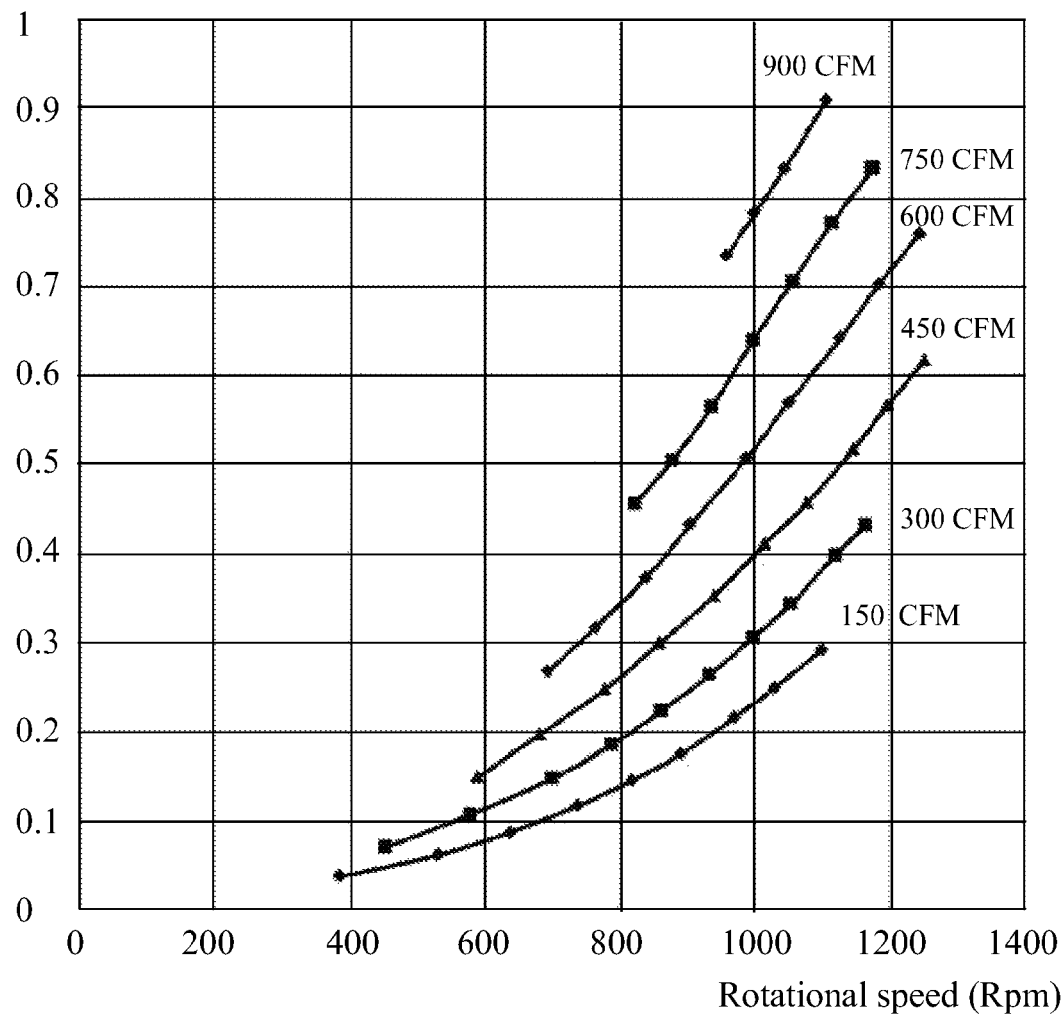
FIG. 8 is fitting curves of constant air volumes of a blower motor acquired from measurement in accordance with one embodiment of the invention.

The mathematical model of the method for controlling the constant air volume by the direct power control of the invention is developed and established as follows: generally speaking, in the air ventilation system, the blower is driven by the blower motor to produce the air flow in a stable state. The constant air volume control is realized by the control of the speed and the power at a static pressure, which satisfies the relation CFM=F(P, speed, pressure), where CFM represents the air volume, P represents the power, speed represents the speed, and pressure represents the static pressure. When the static pressure changes, the constant air volume is maintained by controlling the power and the speed. The power and the speed change with the increase of the static pressure, which is illustrated by the CFM curves of the constant air volume in FIG. 8. Based on the CFM curves, the control model is developed. When the air volume requirement is determined by the product control, the constant air volume CFM is realized by controlling the power and the speed at a certain static pressure. As shown in FIG. 8, the characteristic curve represents the physical property of the constant air volume controlled by the power and the rotational speed. For any designed air flow system in a range of a rated power of the motor based on the test results of the power and the rotational speed curve, a typical second-order function $P=C_1+C_2\times n+C_3\times n^2$ can be used as a typical function for development and modeling. Three undetermined points (A, B, and C) are selected from the curve, corresponding coordinates of these points are (p1,n1), (p2,n2), and (p3,n3), and coefficients thereof are C1, C2, and C3, which satisfy the following equation:

$F(A,B,C)=\Sigma_i^m Yi-(C1+C2*n+C3*n^2))^2$, the equation is solved by $\partial F/\partial A=0$, $\partial F/\partial B=0$, and $\partial F/\partial C=0$, so that $m=3$.

The curve fitting process is selecting the polynomial curve for description. The coefficient of the polynomial can be calculated by the least square method. Theoretically, $P=C_1+C_2\times n+C_2\times n^2+ \ldots +Cm\times n^{m-1}$ is adopted for calculation, but in practice the binomial is adapted to satisfy the general requirement. The function relation P=f(n) is a second-order function, $P=C_1+C_2\times n+C_3\times n^2$, in which $C_1$, $C_2$, and $C_3$ are coefficients, and n is the rotational speed of the motor. In multiple measured target air volume, each target air volume corresponds to a group of coefficients $C_1, C_2$, and $C_3$, and the corresponding relation is stored, so that the corresponding group of the coefficients $C_1$, $C_2$, and $C_3$ is acquired by the microprocessor using the look-up table method according to the input target air volume IN-CFM, thereby obtaining the function relation P=f(n). Each target air volume of a certain load and the corresponding coefficient group thereof $C_1, C_2$, and $C_3$ are listed in Table 1.

TABLE 1

| CFM | $C_1$ | $C_2$ | $C_3$ |
| --- | --- | --- | --- |
| 150 | 0.338 | −0.151 | 0.0458 |
| 300 | 0.4423 | −0.2113 | 0.0765 |
| 450 | ... | ... | ... |
| 600 | ... | ... | ... |
| 750 | ... | ... | ... |
| 900 | ... | ... | ... |

Figure 9:
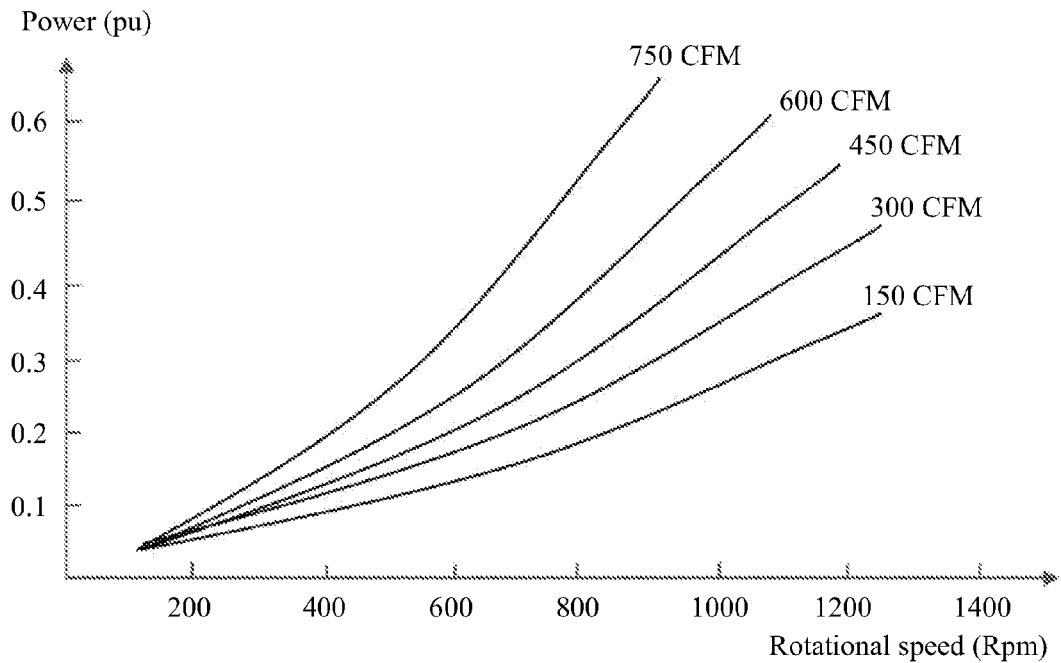
FIG. 9 is fitting curves of experimental data of constant air volumes by direct power control of a ⅓ HP blower motor.

FIG. 9 is fitting curves of experimental data of the constant air volume controlled by the direct power of a ⅓ HP blower motor in a small pipe of the air conditioning system. For a given objective air flow, some typical air volume points CFM are selected by the system as test points to establish a data bank for the mathematical model. The typical air volume points include a minimum air volume and a maximum air volume, and additional middle points are selected according to the product specification. Five typical test points of the air volume CFM are provided, which are 150, 300, 450, 600, and 750 CFM.

An example is illustrated in Table 2 to show the results of the test data. The rotational speed of the motor ranges from 200 to 1400 rpm. The static pressure of the system is between 0.1 and 1 H$_2$O. The output of the preset constant air volume CCFM is maintained so as to acquire a per-unit value of the input power of the motor corresponding to FIG. 9 and to form the data bank.

the requested constant air volume IN-CFM. For example, when the requirement for the requested constant air volume IN-CFM=525 cfm is received, the adjacent two curves CFM1—600 cfm and CFM2—450 cfm are recognized by the model, and the new equation of the curve IN-CFM=525 cfm is calculated by the two corresponding equations. Based on the requested IN-CFM=525 cfm and the three selected rotational speed $\omega$1, $\omega$2, and $\omega$3, the power values at these rotational speeds are calculated. The functions corresponding to the two model curves are utilized to calculate the P

TABLE 2

| 150 CFM air volume | | 300 CFM air volume | | 450 CFM air volume | | 600 CFM air volume | | 750 CFM air volume | |
|---|---|---|---|---|---|---|---|---|---|
| Rotational speed | Power | Rotational speed | Power | Rotational speed | Power | Rotational speed | Power | Rotational speed | Power |
| 385.3 | 3.6% | 452.2 | 6.9% | 590.1 | 14.8% | 693.6 | 26.6% | 822.9 | 45.6% |
| 385.9 | 3.6% | 577.7 | 10.6% | 680.6 | 19.6% | 763.9 | 31.6% | 878.1 | 50.4% |
| 531 | 6.0% | 700.3 | 14.6% | 778.5 | 24.7% | 839.3 | 37.2% | 936 | 56.4% |
| 637.3 | 8.6% | 787.5 | 18.4% | 858.4 | 29.8% | 905 | 43.2% | 997.9 | 63.9% |
| 737.4 | 11.6% | 861.2 | 22.2% | 940.5 | 35.2% | 987.8 | 50.6% | 1056 | 70.5% |
| 818.4 | 14.4% | 932.6 | 26.2% | 1015 | 41.0% | 1051 | 57.0% | 1115 | 77.1% |
| 891 | 17.4% | 997.9 | 30.5% | 1078 | 45.6% | 1127 | 64.1% | 1176 | 83.3% |
| 970.3 | 21.5% | 1053 | 34.2% | 1146 | 51.6% | 1184 | 70.2% | 1173 | 83.2% |
| 1029 | 24.8% | 1119 | 39.7% | 1197 | 56.6% | 1245 | 75.0% | | |
| 1100 | 28.3% | 1165 | 43.1% | 1252 | 61.6% | | | | |
| 1163 | 32.4% | | | | | | | | |

The least square method, the second order function relation between each preset air volume CFM and the corresponding power and rotational speed, is adopted to calculate the power defined by the equation and the rotational speed of the work point of any system under a given static pressure. When the preset air volume IN-CFM is input, a corresponding function is defined by the motor system, and the trace of the work point satisfies the definition of the function. The equations (3)-(7) can be presented by a standard equation, and C1, C2, and C3 are constants.

$$\text{Power}(150) = 0.3388\left(\frac{n}{1000}\right)^2 - 0.1551\left(\frac{n}{1000}\right) + 0.0458 \quad (3)$$

$$\text{Power}(300) = 0.4423\left(\frac{n}{1000}\right)^2 - 0.2113\left(\frac{n}{1000}\right) + 0.0765 \quad (4)$$

$$\text{Power}(450) = 0.3987\left(\frac{n}{1000}\right)^2 - 0.0308\left(\frac{n}{1000}\right) + 0.0294 \quad (5)$$

$$\text{Power}(600) = 0.2580\left(\frac{n}{1000}\right)^2 + 0.3983\left(\frac{n}{1000}\right) - 0.1379 \quad (6)$$

$$\text{Power}(750) = 0.1385\left(\frac{n}{1000}\right)^2 + 0.8150\left(\frac{n}{1000}\right) - 0.3139 \quad (7)$$

Thus, $P=C_1+C_2 \times n+C_3 \times n^2$ is obtained. The established curves of the equations (3)-(7) provide five traces for the selected work points required by the five constant air volumes CFM.

Figure 10:
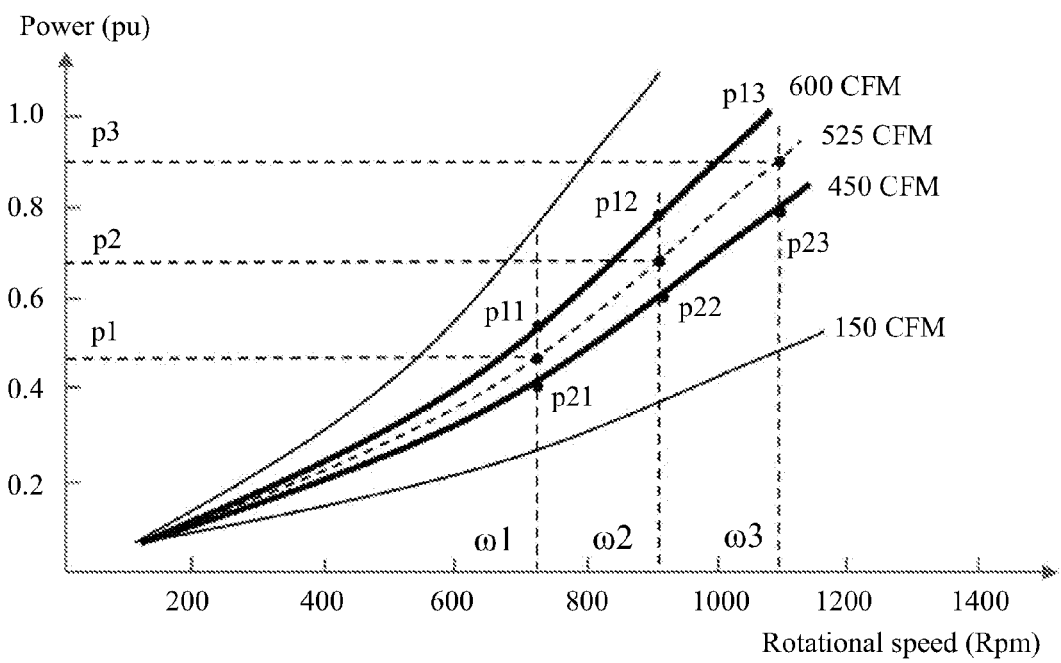
FIG. 10 is fitting curves of experimental data for calculating any input air volume of a blower motor by interpolation.

As shown in FIG. 10, if the requested constant air volume IN-CFM is not any of the modeled curves, the interpolation method is used to acquire a new characteristic equation to fit value for selected speed of the double power points by the linear weighted interpolation. Firstly, matrix data are listed as follows:

$$\begin{bmatrix} P_i \\ P_1(600) \\ P_2(450) \end{bmatrix} = \begin{bmatrix} \omega_1 & \omega_2 & \omega_3 \\ P_{11} & P_{12} & P_{13} \\ P_{21} & P_{22} & P_{23} \end{bmatrix}$$

One power point $(p_{1i}, p_{2i})$ corresponds to a selected speed $\omega$, and the selected speed $\omega$1, $\omega$2, and $\omega$3 correspond to three groups of power points $(p_{1i}, p_{2i})$, and the linear weighted interpolation value can be used to calculate the $P_i$ according to the equation $pi=p_{2i}+w \cdot (p_{1i}-p_{2i})$. The weighted value W is calculated as follows:

$$w = \frac{CFM - CFM2}{CFM1 - CFM2}.$$

It should be noted that CFM2≤IN-CFM≤CFM1, and 0≤W≤1. The following matrix equation is calculated as follows:

$$\begin{bmatrix} \omega_1^2 & \omega_1 & 1 \\ \omega_2^2 & \omega_2 & 1 \\ \omega_3^2 & \omega_3 & 1 \end{bmatrix} \begin{bmatrix} C_1 \\ C_2 \\ C_3 \end{bmatrix} = \begin{bmatrix} P_1 \\ P_2 \\ P_3 \end{bmatrix}$$

Thus, the function $P=C_1+C_2\times n+C_3\times n^2$ corresponding to IN-CFM=525 cfm can be acquired. Coefficients C1, C2, and C3 can be calculated by solving the matrix equation. Thus, the power equation can be acquired for any request input air volume IN-CFM. Since such process is accomplished in the microprocessor-MCU in the motor controller, the power calculation does not consume much real-time CPU resource.

It is known that the direct power control adopts the rotational speed control to reach the power control. The control logic of the power/rotational speed functions in coordinating the time constant of the power/rotational speed circuit to ensure the stability of the system. The control can be realized by the accuracy control of the motor and the comparison of the torque control. The speed control is much effective than the torque control under either the vector control or the scalar control, thereby improving the control accuracy.

Figure 12:
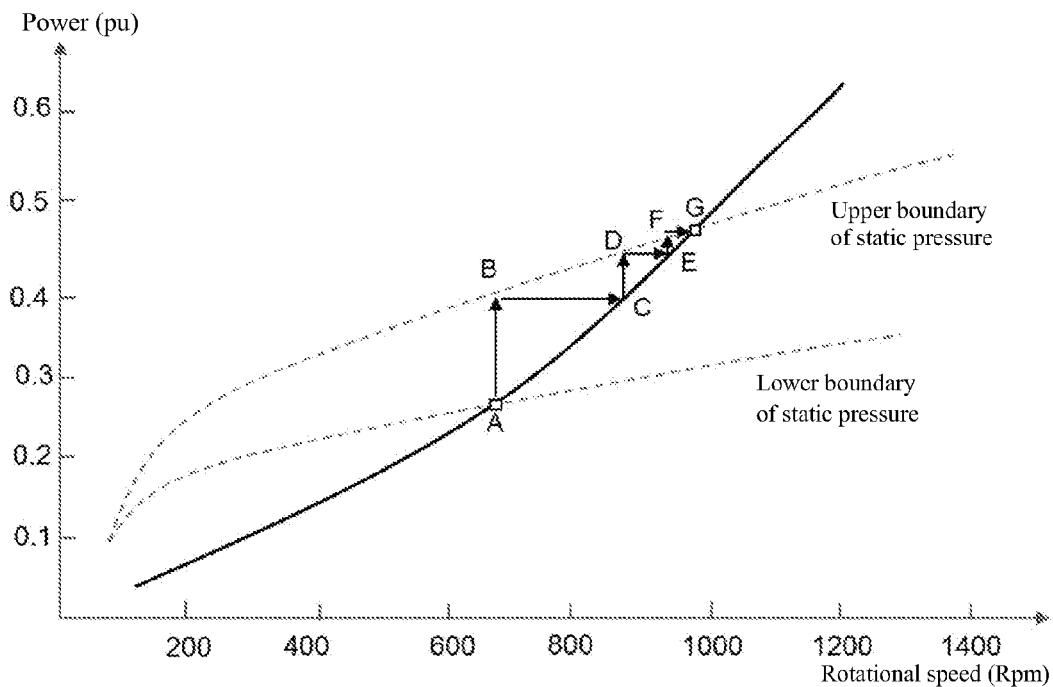
FIG. 12 is a diagram showing a first control process of a method for controlling a constant air volume of a blower motor in accordance with one embodiment of the invention.

The DPC control realizes the speed control by the unique power feature and the speed feature of the blower load. The rotational speed increases from zero to a certain value, while the power correspondingly increases from zero. The rotational speed of the motor increases to a certain work point A (power, speed), which is a static pressure point, as shown in FIG. 12. When the static pressure suddenly increases under the speed control mode, the motor provides a higher power (or a larger toque) to keep the speed because the relatively higher static pressure requires a great power. The power will increase to a much higher degree, and when the motor system reaches a new work point B at the same rotational speed, whether the work point B is on the constant CFM trace is known by the algorithm, thereby determining a pair of power/speed point C. However, the point C is not a stable work point. To satisfy the requirement of the high power, a D point is reached, the above steps are repeated until a new stable work point G is reached by equiconvergence, and the process is finished.

Figure 13:
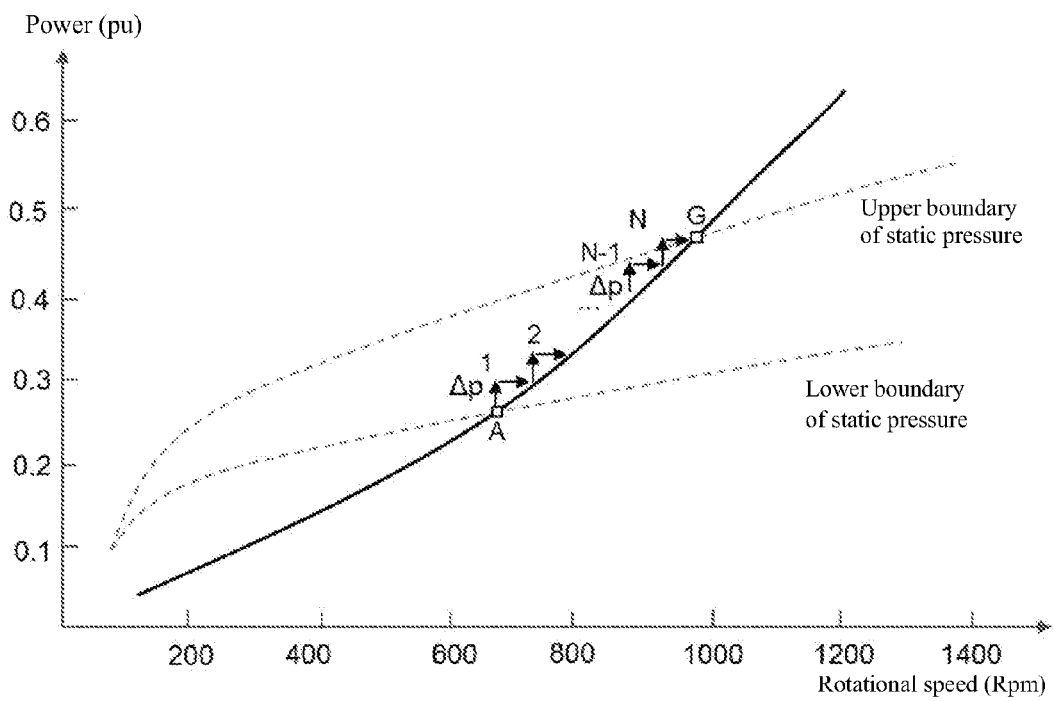
FIG. 13 is a diagram showing a second control process of a method for controlling a constant air volume of a blower motor in accordance with one embodiment of the invention.

In the example, the restricted control of the power increase is adopted in case of sudden variation of the power fluctuation. As shown in FIG. 13, the power increase can be defined as ΔP. As long as the power variation exceeds the power increase ΔP, the speed control is executed. In such mode, all the work points work under a positive and negative bandwidth of a corresponding CFM trace of the constant air volume. The air flow control system is stable during the transitional process of the static pressure variation.

Figure 14:
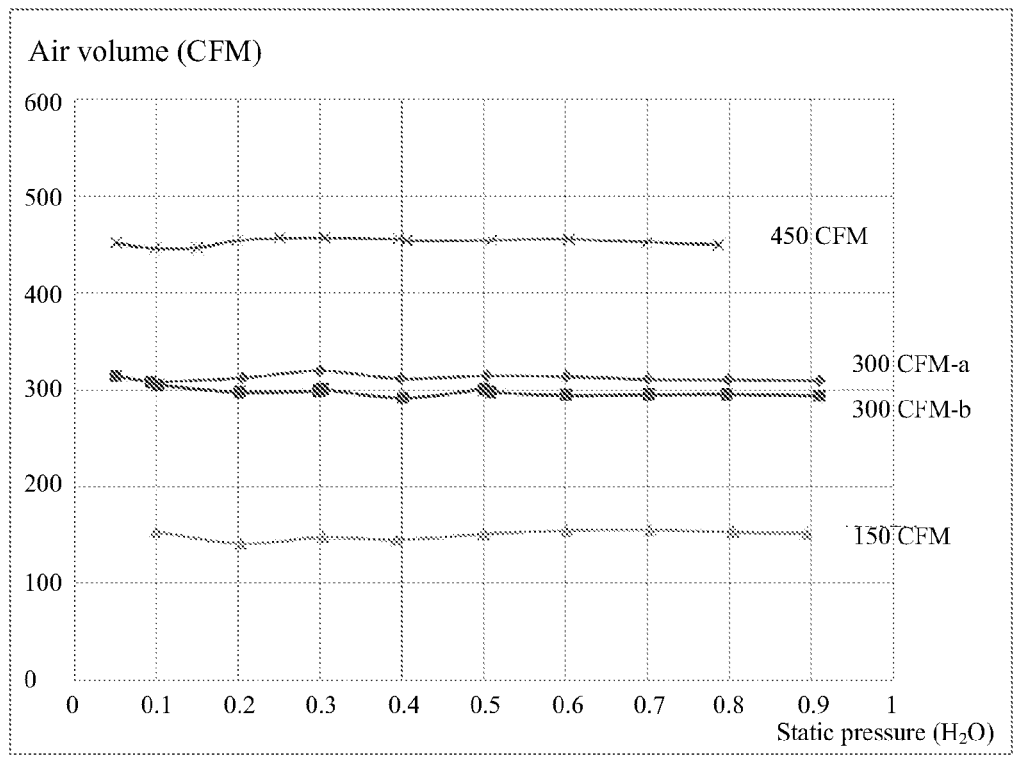
FIG. 14 is a diagram showing test results of a method for controlling a constant air volume of a blower motor demonstrated by experiments in accordance with one embodiment of the invention.
Figure 15:
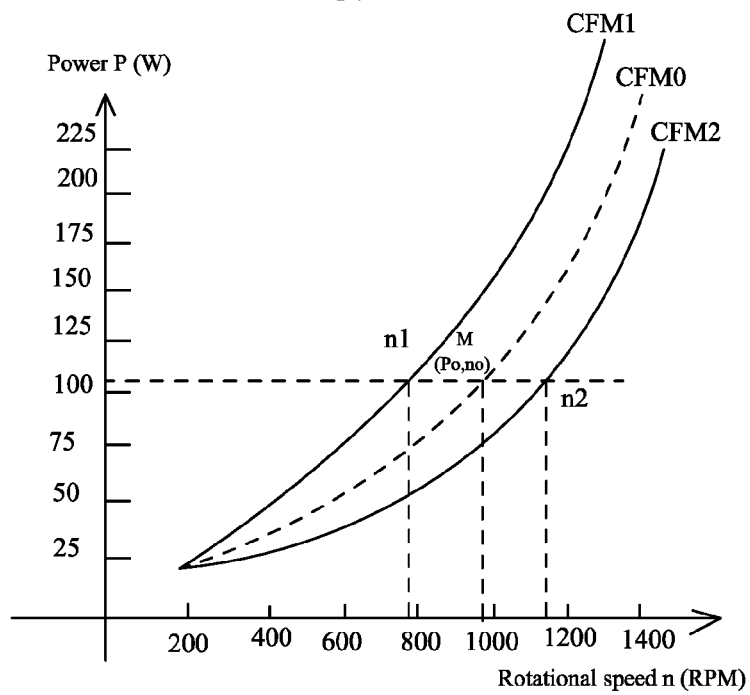
FIG. 15 is a schematic diagram showing calculation of an air volume of a motor blower in accordance with one embodiment of the invention.
Figure 16:
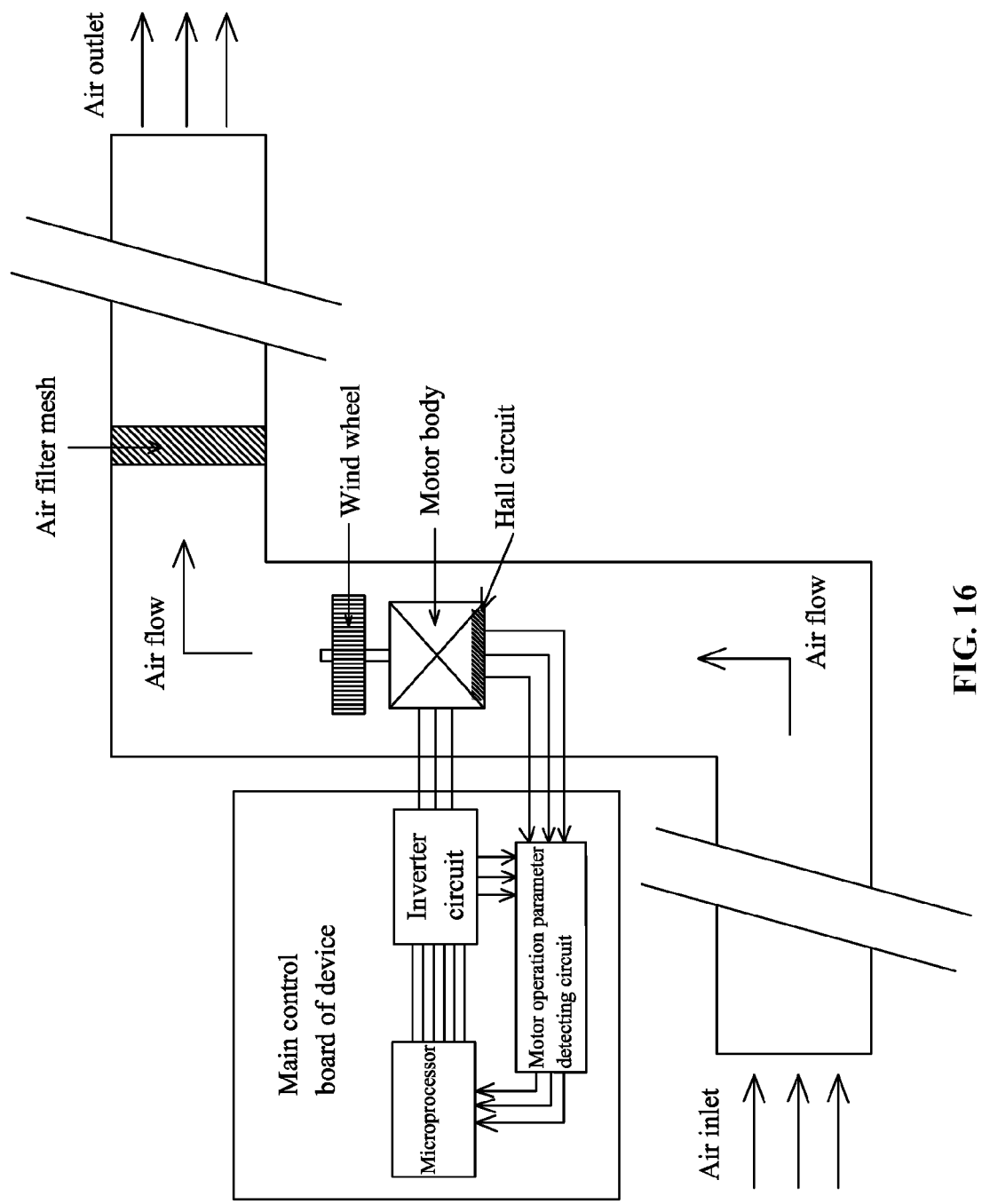
FIG. 16 is a structure diagram of a device of Example 2.

As shown in FIG. 14, the above method and the algorithm for controlling the constant air volume by the direct power control have been tested on the blower motor controller, and all the performances of the system satisfy the requirements of FIG. 15.

Figure 11:
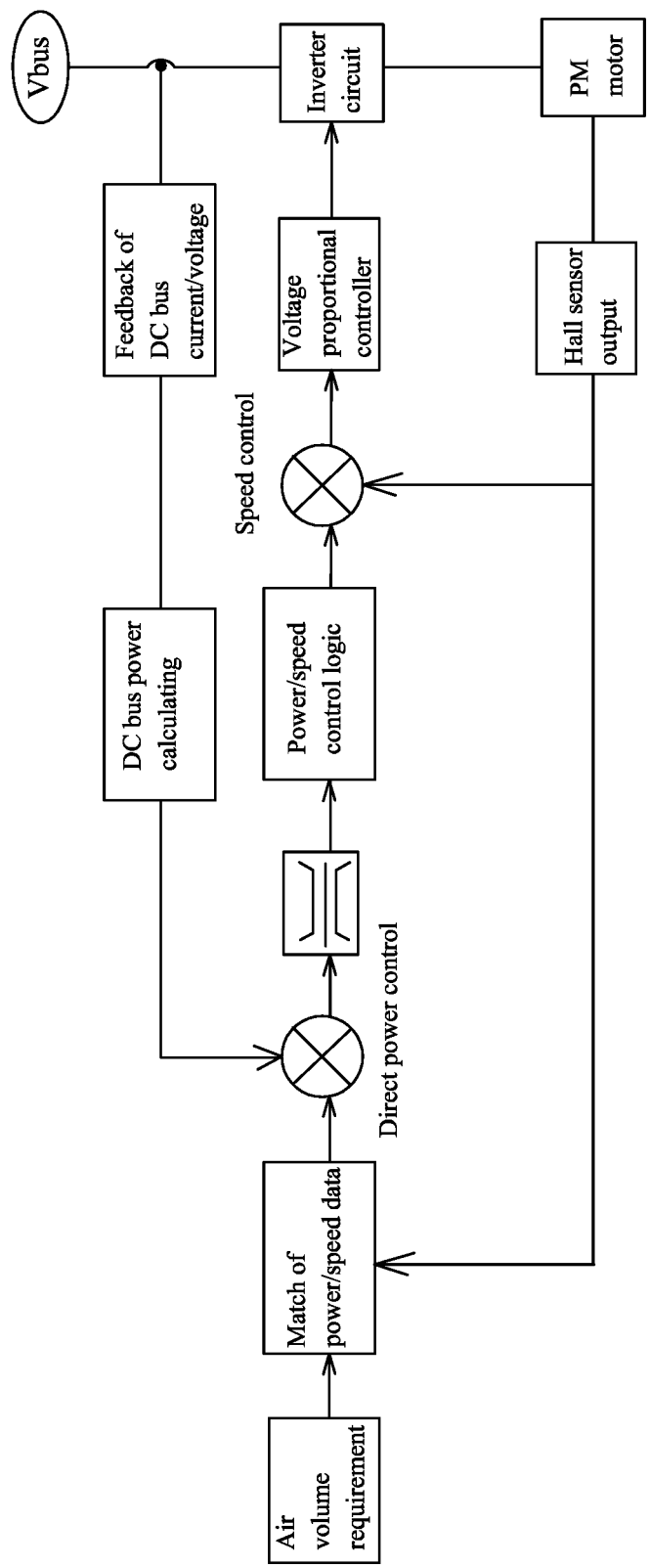
FIG. 11 is a control logic diagram of a method for controlling a constant air volume of a blower motor in accordance with one embodiment of the invention.

FIG. 11 is a logic block diagram showing the application of the scalar control of the blower motor. The input power is acquired under the DC bus voltage and current. The power and the rotational speed are limited within the maximum power $P_{max}$ and the maximum rotational speed $n_{max}$.

The real-time input power value $P_i$ of the motor is calculated by the feedback DC bus current/voltage, and based on the match of the target air volume IN-CFM input from the external and the power/speed data, the calculated value $P_t$ of the input power of the motor is acquired. The calculated value $P_t$ of the input power of the motor is then compared with the real-time output power $P_i$ of the motor to acquire a power difference ΔP which is limited within a certain range thereby being prevented from being too large and avoiding the relatively large fluctuation of the power. The power difference ΔP is output by the power/speed control logic for conducting the speed loop control, and the rotational speed control is carried out by the PWM frequency inverter. The scalar control is adopted, that is, the real-time input power $P=I_{bus}\times V_{bus}$ is calculated based on the collected real-time bus current $I_{bus}$ and real-time bus voltage.

Principle for measuring the air volume of the blower motor is as follows:

Based on the above theoretical analysis: FIG. 9 is a chart showing the fitting curves of the experimental data of the constant air volume by the direct power control of a ⅓HP blower motor in an air conditioning system provided with a small pipe, five test points of the air volume CFM are provided, which are respectively 150, 300, 450, 600, and 750 CFM, and equations (3)-(7) are acquired. Table 2 is an example showing the test data results. The rotational speed of the motor is in a range of between 200 and 1400 rpm. The static pressure of the system ranges from 0.1 to 1 $H_2O$, the output of the preset air volume CCFM is maintained, and the per-unit value of the input power of the motor corresponding to FIG. 9 is acquired. Air volume data input that does not belong any of the above 5 work points are described, for example, the function $P=C_1+C_2\times n+C_3\times n^2$ of IN-CFM=525 cfm is acquired. The coefficients $C_1$, $C_2$, and $C_3$ can be calculated when the matrix equation is solved. Thus, for any requested input air volume IN-CFM, the power equation can be acquired, that is, for any input target air volume, the function $P=C_1+C_2\times n+C_3\times n^2$ for the constant air volume control corresponding to the target air volume can be acquired.

According to backward reasoning of the above principle, when the motor operates in the stable state, the real-time power $P_0$ and the rotational speed $n_0$ are measured, as shown in FIG. 15, based on the point $M(P_0, n_0)$, the curve $CFM_0$ of the constant air volume control at the point $M(P_0, n_0)$ can be derived, and therefore the air volume corresponding to the point $M(P_0, n_0)$ can be known. The derivation process is as follows:

The curve $CFM_0$ is arranged between the above two known air volume curves. $P_0$ is substituted into the equations (3)-(7), the rotational speeds n(150), n(300), n(450), n(600), and n(750) corresponding to the five air volumes are obtained. By comparing the rotational speed, two known air volume curves between which the rotational speed n0 is disposed are determined. Presuming that the point $M(P_0, n_0)$ is disposed between the constant air volume curves $CFM_1$ and $CFM_2$, in condition that the input power is equal to $P_0$, the rotational speeds corresponding to the constant air volume curves $CFM_1$ and $CFM_2$ are respectively $n_1$ and $n_2$, then the constant air volume point of the point $M(P_0, n0)$ is $CFM_0=CFM_2+(CFM_1-CFM_2)\times(n_2-n_0)\div(n_2-n_1)$, in which, $CFM_1$ and $CFM_2$ are two of the five air volumes 150, 300, 450, 600, and 750. It is known from the above derivation, the air volume point $CFM_0$ output by the air conditioning system can be derived based on the know real-time power $P_0$ and the rotational speed $n_0$ of the motor, and when the detected air volume is a certain degree lower than the variance of the preset air volume, it is determined that the air filter mesh is obstructed and an alarm signal is output.

Example 2

Figure 17:
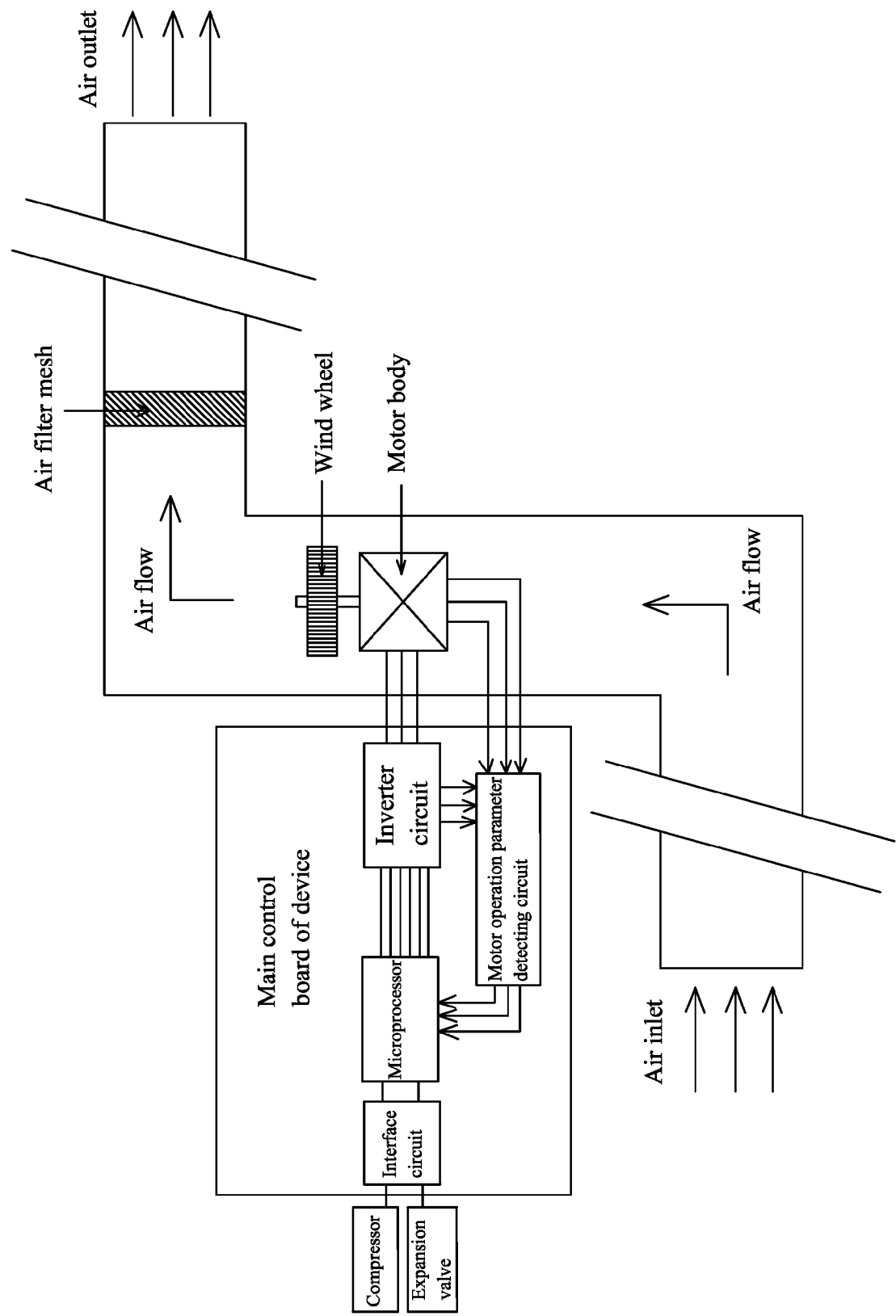
FIG. 17 is a structure diagram of an air conditioning system of Example 3.

A device for detecting blockage of an air filter mesh is shown in FIG. 17, the device comprises: an air inlet, an air outlet, an air duct, a fan or a wind wheel, a blower motor, an air filter mesh, and a controller. The air filter mesh is disposed in the air duct. The blower motor drives the fan or the wind wheel to rotate to allow the air to enter the air duct via the air inlet, pass through the air filter mesh, and exit the air duct via the air outlet. The blower motor is a motor body excluding a controller and comprises: a rotating shaft, a permanent magnetic rotor assembly, a stator assembly, and a housing assembly. The permanent magnetic rotor assembly and the stator assembly form magnetic coupling. The stator assembly comprises a stator core and a coiling winding wound on the stator core. The motor body further comprises a Hall circuit for detecting a rotor position signal. The controller of the device comprises a main control board, and the main control board comprises: a microprocessor, an inverter circuit, and a motor operation parameter detecting circuit. An output terminal of the inverter circuit is connected to the coil winding. The motor operation parameter detecting circuit inputs a real time operation parameter into the microprocessor, and an output terminal of the microprocessor controls the inverter circuit. The microprocessor comprises a function module for calculating an air volume, and the function module calculates a detected air volume according to the real time operation parameter. When the detected air volume is smaller than a preset air volume, the microprocessor determines that the air filter mesh is obstructed and outputs a signal to an alarm circuit to trigger an alarm.

The real time operation parameter of the motor comprises: a phase current and a rotor position signal; or a bus current and a rotor position signal; or a bus current, a bus voltage, and a rotor position signal. The motor body is utilized as a unit for detecting the air volume. When a difference between the detected air volume and the preset air volume reaches a certain value, it is determined that the air filter mesh is obstructed and the alarm is triggered. The blower motor operates in a mode of constant air volume control. The microprocessor firstly measures a real time power to determine whether the real time power reaches a rated power. When the real time power reaches the rated power, a difference between the detected air volume and the preset air volume is then determined. When the detected air volume is smaller than 90% of the rated air volume, it is determined that the air filter mesh is obstructed. When the difference between the detected air volume and the preset air volume reaches a certain value, the microprocessor controls the alarm circuit to trigger the alarm which indicates that the air filter mesh is obstructed. The alarm circuit is an audio alarm circuit or a photoelectric alarm circuit. The alarm circuit is arranged in the controller of the device.

Example 3

An air conditioning system, as shown in FIG. 18, comprises a conditioner body. a compressor, an expansion valve, a blower motor, a wind wheel, an air filter mesh, and a control board of the air conditioning system is disposed in the conditioner body. The conditioner body also provided with an air duct. The air duct comprises an air inlet and an air outlet. An air filter mesh and a wind wheel are mounted in the air duct. The blower motor drives the wind wheel to rotate. The blower motor adopts a brushless direct current (BLDC) motor or an electronically commutated (ECM) motor and comprises a motor body. The motor body comprises: a rotating shaft, a permanent magnetic rotor assembly, a stator assembly, and a housing assembly. The permanent magnetic rotor assembly and the stator assembly form magnetic coupling. The stator assembly comprises a stator core and a coiling winding wound on the stator core. The control board of the air conditioning system comprises: a microprocessor, an inverter circuit, and a motor operation parameter detecting circuit. An output terminal of the inverter circuit is connected to the coil winding. The motor operation parameter detecting circuit inputs a real time operation parameter into the microprocessor, and an output terminal of the microprocessor controls the inverter circuit. The microprocessor is connected to the compressor and the expansion valve via an interface circuit for controlling the compressor and the expansion valve. The motor body is utilized as a unit for detecting the air volume. When a difference between the detected air volume and the preset air volume reaches a certain value, it is determined that the air filter mesh is obstructed and the alarm is triggered. The air conditioning system is a split air conditioner, a cabinet air conditioner, a window air conditioner, a multi-connected air conditioner, a wind pipe air conditioner, a commercial coil air conditioner, a ceiling air conditioner, a heating, ventilating, and air conditioning system, a living air device, an air cleaner, or a soot absorber.

It can be preset that when the detected air volume is smaller than 90% of the preset air volume, it is determined that the air filter mesh is obstructed. The control board inputs the preset air volume to the blower motor. The microprocessor detects the air volume in real time. When a difference between the detected air volume and the preset air volume reaches a certain value, the microprocessor controls the alarm circuit to trigger the alarm which indicates that the air filter mesh is obstructed. The alarm circuit is an audio alarm circuit or a photoelectric alarm circuit. The alarm circuit is arranged on the control board of the air conditioning system. The alarm circuit comprises a liquid crystal display. The microprocessor sends the alarming signal to the control board, and the control board outputs a signal to the liquid crystal display to indicate that the air filter mesh is obstructed in the form of characters or figures. The blower motor can operate in a mode of constant air volume control. The microprocessor firstly measures a real time power to determine whether the real time power reaches a rated power. When the real time power reaches the rated power and a difference between the detected air volume and the preset air volume reaches a certain value, the alarm is triggered. When the difference between the detected air volume and the preset air volume is within a permitted range, the alarm is not triggered. The blower motor can also operate in a mode of constant torque control, and when a difference between the detected air volume and the preset air volume reaches a certain value, it is determined that the air filter mesh is obstructed and the alarm is triggered. The blower motor can also operate in a mode of constant rotational speed control, and when a difference between the detected air volume and the preset air volume reaches a certain value, it is determined that the air filter mesh is obstructed and the alarm is triggered.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:
1. A device for detecting blockage of an air filter mesh, the device comprising:
 a) an air inlet;
 b) an air outlet;
 c) an air duct;
 d) a fan or a wind wheel;

e) a blower motor, the blower motor comprising: a rotating shaft, a permanent magnetic rotor assembly, a stator assembly, and a housing assembly; the stator assembly comprising a stator core and a coiling winding;

f) the air filter mesh; and g) a controller, the controller comprising a main control board comprising: a microprocessor, an inverter circuit, and a motor operation parameter detecting circuit; the inverter circuit comprising an output terminal; the microprocessor comprising an output terminal and a function module for calculating an air volume;

wherein the air filter mesh is disposed in the air duct; the blower motor drives the fan or the wind wheel to rotate to allow the air to enter the air duct via the air inlet, pass through the air filter mesh, and exit the air duct via the air outlet;

the blower motor is a motor body excluding a controller; the permanent magnetic rotor assembly and the stator assembly form magnetic coupling; the coiling winding is wound on the stator core;

the output terminal of the inverter circuit is connected to the coil winding; the motor operation parameter detecting circuit inputs a real time operation parameter into the microprocessor, and the output terminal of the microprocessor controls the inverter circuit; the function module calculates a detected air volume according to the real time operation parameter; and when the detected air volume is smaller than a preset air volume, the microprocessor determines that the air filter mesh is obstructed and outputs a signal to an alarm circuit to trigger an alarm.

2. The device of claim 1, being a split air conditioner, a cabinet air conditioner, a window air conditioner, a multi-connected air conditioner, a wind pipe air conditioner, a commercial coil air conditioner, a ceiling air conditioner, a heating, ventilating, and air conditioning system, a living air device, an air cleaner, or a soot absorber.

3. The device of claim 1, wherein the real time operation parameter of the motor comprises: a phase current and a rotor position signal; or a bus current and a rotor position signal; or a bus current, a bus voltage, and a rotor position signal.

4. The device of claim 3, wherein a function for calculating the air volume is Q=F(POWER, n), in which, POWER represents an input power of the motor and is calculated by the bus current and the bus voltage of the motor, n represents a rotational speed of the motor and is calculated by the rotor position signal.

5. The device of claim 1, wherein the blower motor operates in a mode of constant air volume control;

the microprocessor firstly measures a real time power to determine whether the real time power reaches a rated power;

when the real time power reaches the rated power and a difference between the detected air volume and the preset air volume reaches a certain value, the alarm is triggered; and when the difference between the detected air volume and the preset air volume is within a permitted range, the alarm is not triggered.

6. The device of claim 2, wherein the blower motor operates in a mode of constant air volume control;

the microprocessor firstly measures a real time power to determine whether the real time power reaches a rated power;

when the real time power reaches the rated power and a difference between the detected air volume and the preset air volume reaches a certain value, the alarm is triggered; and when the difference between the detected air volume and the preset air volume is within a permitted range, the alarm is not triggered.

7. The device of claim 3, wherein the blower motor operates in a mode of constant air volume control;

the microprocessor firstly measures a real time power to determine whether the real time power reaches a rated power;

when the real time power reaches the rated power and a difference between the detected air volume and the preset air volume reaches a certain value, the alarm is triggered; and when the difference between the detected air volume and the preset air volume is within a permitted range, the alarm is not triggered.

8. The device of claim 1, wherein the blower motor operates in a mode of constant torque control, and when a difference between the detected air volume and the preset air volume reaches a certain value, it is determined that the air filter mesh is obstructed and the alarm is triggered.

9. The device of claim 2, wherein the blower motor operates in a mode of constant torque control, and when a difference between the detected air volume and the preset air volume reaches a certain value, it is determined that the air filter mesh is obstructed and the alarm is triggered.

10. The device of claim 3, wherein the blower motor operates in a mode of constant torque control, and when a difference between the detected air volume and the preset air volume reaches a certain value, it is determined that the air filter mesh is obstructed and the alarm is triggered.

11. The device of claim 1, wherein the blower motor operates in a mode of constant rotational speed control, and when a difference between the detected air volume and the preset air volume reaches a certain value, it is determined that the air filter mesh is obstructed and the alarm is triggered.

12. The device of claim 2, wherein the blower motor operates in a mode of constant rotational speed control, and when a difference between the detected air volume and the preset air volume reaches a certain value, it is determined that the air filter mesh is obstructed and the alarm is triggered.

13. The device of claim 3, wherein the blower motor operates in a mode of constant rotational speed control, and when a difference between the detected air volume and the preset air volume reaches a certain value, it is determined that the air filter mesh is obstructed and the alarm is triggered.

14. The device of claim 2, wherein the main control board is a control board of the air conditioning system; and the microprocessor of the main control board is connected to a compressor and an expansion valve via an interface circuit for controlling the compressor and the expansion valve.

15. The device of claim 14, wherein the alarm circuit is an audio alarm circuit or a photoelectric alarm circuit.

16. The device of claim 15, wherein the alarm circuit comprises a liquid crystal display; and the microprocessor outputs a signal to the liquid crystal display to indicate that the air filter mesh is obstructed in the form of characters or figures.

17. The device of claim 3, wherein the motor body further comprises a Hall circuit for detecting a rotor position signal.

* * * * *